United States Patent [19]

Malecki

[11] Patent Number: 4,587,213

[45] Date of Patent: May 6, 1986

[54] METHODS AND MEANS OF DETERMINING MICROORGANISM POPULATION

[76] Inventor: George J. Malecki, P.O. Box 647, St. Augustine, Fla. 32085

[21] Appl. No.: 214,637

[22] Filed: Apr. 9, 1981

Related U.S. Application Data

[63] Continuation-in-part of Ser. No. 401,379, Dec. 23, 1953, abandoned, and a continuation-in-part of Ser. No. 252,600, Jan. 21, 1963, abandoned, and a continuation-in-part of Ser. No. 516,827, Nov., 1965, abandoned, and a continuation-in-part of Ser. No. 77,881, Oct. 3, 1970, abandoned, and a continuation-in-part of Ser. No. 711,057, Aug. 2, 1976, abandoned, and a continuation-in-part of Ser. No. 886,841, Mar. 29, 1978, abandoned.

[30]  Foreign Application Priority Data

Sep. 29, 1971 [GB] United Kingdom ............... 45337/71

[51] Int. Cl.$^4$ .......................... C12Q 1/06; C12Q 1/08; C12M 1/26; C12M 1/20
[52] U.S. Cl. ........................................ 435/39; 435/40; 435/292; 435/301
[58] Field of Search .................... 435/39, 40, 292, 301

[56]  References Cited

U.S. PATENT DOCUMENTS

| 2,672,431 | 3/1954 | Goetz | 435/299 |
| 2,677,646 | 5/1954 | Lovell et al. | 435/297 |
| 2,677,647 | 5/1954 | Lovell | 435/297 |
| 2,761,813 | 9/1956 | Goetz | 435/299 |

OTHER PUBLICATIONS

Gershenfeld, Bacteriology and Allied Subject, pp. 77 to 79.
Abbott, Principles of Bacteriology 2nd Ed., pp. 68–72 and 101–110 (1894).

*Primary Examiner*—Alvin E. Tanenholtz

[57]  ABSTRACT

The described method of determining viable microorganism population comprises spreading an experimentally pre-determined volume of an aqueous suspension of said microorganism, (such as bacteria, ricketsia, yeasts, fungi, molds, algae, viruses, protozes and similar organism), on the surface of a dried hydrophilic polymer film, capable of forming a solid (non-flowing) gel on rehydration and supported by a suitable (for subsequent operations) piece of material, (made of glass, ceramic, metal, plastic etc.), adaptable for coating, drying, and examining, said hydrophilic film with or without nutrient for said microorganisms and optionally containing a coloring matter capable to discolor, when in the vicinity of said viable microorganisms, which film by imbibing free water from the said suspension, functions as a filter to retain and distribute the microorganism content as a deposit on the surface of said film, (with or without natural nutrient present in said suspension), then incubating the microorganism deposit, whereby said microorganisms grow in colonies and determining the microorganism population by counting said colonies, or, if said coloring matter was included in said film, then determining said microorganism population measuring the time period during which said ratios of said coloring matter appears or by measuring the discoloration degree of said coloring matter in transmitted or reflected light, or alternatively counting said discolored colonies.

11 Claims, No Drawings

METHODS AND MEANS OF DETERMINING MICROORGANISM POPULATION

The present specification and claims constitute the continuation-in-part application in regard to the following prior patent applications:

Ser. No. 401,379 filed on Dec. 23, 1953 for the "Method and Means for Counting Bacteria", now abandoned.

Ser. No. 252,600 filed Jan. 21, 1963, for the "Method and Mrans for Counting Bacteria", now abandoned.

Ser. No. 516,827 filed Nov. 26, 1965 and now abandoned, for "Method and Means for Counting Bacteria", allowed with 5 claims allowed on Nov. 1, 1978.

Ser. No. 77881 filed Oct. 3, 1970 for "Rapid determination of Microorganisms Population" now abandoned.

Ser. No. 711,057 filed Aug. 2, 1976 which is now abandoned, and Ser. No. 886.841 filed Mar. 29, 1978 for "Methods and Means of Determining Microorganism Population", now abandoned.

The present methods in general use for counting viable microorganisms in food, water and on food equipment as well as in medical fluids are not only cumbersome but also very long. The recent rapid methods of bacteriuria (mainly) detection in doctor's office provide in general only very approximate data without count as provided by the standard plate method. On the other hand modern methods based on chromatography, microcalorimetry, impedance measurement, fluorescent microscopy, radioimmunoassay, computers application, etc. are remarkably reliable and rapid, but require in most cases expensive instrumentation and well trained service personnel. The development of a fast, convenient, and using simple equipment (proferably disposable) method, somewhat similar to the standard agar plate would be a real contribution to the food industry and sanitation authorities, particularly if it will enable the determination of bacterial population the same day (even if only a rough estimate would be given).

Before proceeding to the description of the invention some expressions used often in the description should be defined and elucidated. The term "bacteria" in this specification means any kind of microorganisms. The term "determination" used in the description to follow means: determination, estimation, identification, counting, detection, evaluation, and supplying any information on the amount or kind of bacteria, yeasts, molds, algae, viruses, ricketsia, or other microorganisms present. By the term "counting" is also meant—evaluating or estimating. The term "discoloration" used in the description means change of color into another color, loss of color (transition into white color), darkening of color (including blackening), Fluorescence, etc., or any other color modification capable to be detected with the eye or with an optically sensitive instrument. By the term "microorganism" or "bacteria" in the above and following description and claims is meant viable microorganisms unless otherwise specifically indicated. By the term "dye" in the above or following description and claims is meant any coloring matter which is capable of discoloring in the presence of living microorganisms and is nontoxic to microorganisms under test at employed concentrations. The term "solid" used to describe the medium in given in bacteriological literature, meaning not really solid medium but gelled one and nonflowing or solidified by the gelling action of a suitable polymer (I like agar, or gelatine). The term "known volume" in claims and the specification includes not only an actually measured volume (pipetted volume), but also the approximate volume absorbed during dipping treatment, this volume usually determined more or less accurately from blank tests.

There were many attempts to improve the standard plate test and in particular to develop a short evaluation test, such as Frost Little Plate test, Methylebe blue test, resazurin, Membrane filter technique, Bacto-strip test, and several recent dip-slide tests intended for office use by Doctors. None of them, however allowed for doing the screening test and more exact counting of bacteria from the same sample, with the possibility of incubating the dip-slide from the body heat (by carrying thr container in the pocket), thus eliminating the problem of delivering the milk or urine sample to the laboratory for testing, the problem being that inevitably the bacteria population in the sample during the delivery increased enormously if the delivery was longer than 8–10 hours, as it usually is (even much longer if by post).

The principal object of the present invention is the method of distributing, depositing, and incubating of microorganisms in an aqueous liquid sample (milk etc.) on the surface of initially dehydrated gel of a polymer, whereby a miniature agar plate is formed on which bacteria grow in colonies enabling the perfirmance of a bacteria count, while at the same time a portion of the sample being tested is absorbed by the absorbent material (filter paper or glass fiber filter) containing the dye capable to discolor in the presence of microorganisms (such as 2-3-5 triphenyl tetrazolium chloride), said material being attached to the agar film and the slide and is undergoing rapid discoloration depending on the amount of bacteria in the sample, thus acting as a screening device for large bacteria population, while the remaining surface of the agar film provides the possibility of doing if necessary the more exact count of colonies being grown on this surface.

Another object of the present invention is the method and means for total (dead and viable) bacteria in food, on food equipment and in medicine as well as in polluted water and sewage without the need for cleaning the Petri dish plate, preparation of the nutrient for bacteria, and cleaning the equipment and sterilization of the same, with more assurance of uniform spreading of bacteria suspension over the surface of the coated slide and making the mifroorganisms better visible under the microscope, than is possible at the present time. Furthermore the object of the present invention is the method and means for counting, (determining the population), of viable (living) microorganisms in foods, (milk), water, on food handling equipment, and in medical materials, and sewage, much faster, and more conveniently, than the most used method of standard agar plate (in Petri dishes).

Other objects will be discussed further down within this specification.

The ghist of the present invention resides in the novel inoculation, depositing and distribution method consisting in the use of a microscopic slide (or other suitable device capable to support the agar film) coated with a dehydrated film of a hydrophilic polymer, capable to form a solid gel on rehydration from a dry state, on which surface the dispersion of microorganisms to be examined is spread, so that the hydrophilic polymer absorbs the free, liquid water from said dispersion and the said microorganisms are filtered-off, distributed and deposited on said film's surface devoid of free liquid water, thus becoming exceptionally well visible under microscope as well as fixed immobilized on said surface and capable of growing in colonies.

It is possible to use another absorbing substances instead of a gelled polymer as indicated above. Namely on absorbent filter paper made from cellulose or absorbent sheets made from glass fibers can be employed for rough estimates. Both these substances are porous materials having pores arranged in three dimensional pattern not like the membrane filter which are distributed in a flat, (two dimensional), space pattern. While the above filtering material with pores arranged three dimensionally absorb considerable amount of moisture and retain it by means of capilary forces. The two dimensional filtering materials retain comparatively little of the absorbed aqueous solutions, (as compared to the pure cellulose filters), and thus are not very suitable for the here described purposes. The most convenient way to use these absorbing materials is to attach them to the support, (such as glass slide 1×3" in size or plastic slide), by means of agar gel (attaching to the slide by pouring hot liquid agar first on the slide and then put the absorbing material, (also 1×3" or smaller in size), on top of the liquid agar and let agar set in this position, thus gluing the absorbing material to the slide. These polymer-free absorbing materials are used only for screening purposes as described above because their inherent texture make impossible to make observations on the morphology and other details of the microorganisms. Also counting is not possible because of the fibrous texture of porous absorbing materials. Furthermore the pore size of these absorbing filtering materials is of the size one micron approximately and they retain during filtering particles not smaller than one micron, while the pore size of a 3% agar film (surface) is about 4.7 millimicrons, (see J. Alexander the book "Colloid Chemistry" volume 6), so there is a difference of several orders of magnitude. The agar of 10-20% (as encountered in the rehydrated agar film on our miniplate has still smaller pore size of about (by extrapopovulation of a fraction of a millimicron. All these differences in the purpose and properties of these absorbing materials make them not equivalent and inferior to to the gelled polymers (like agar), and I have the intention to separate patent application later on and for the same reason I am not putting any claims covering the application of these materials used without copolymers only for screening purposes.

Furthermore it is possible to coat by dipping both sides of the microscopic slide into the same melted agar 3% and allow for its gelling and drying as described above. Agar may or may not contain nutrients for bacteria and if the inoculation is done with bacteria suspension containing already nutrient in adequate amount (as for instance milk not diluted, or a suspension of meat desintegrated) then the addition of nutrients to the agar before coating is superfluous. These double-coated slides require special standa or some means to keep them upright or hanging so that neither side of the agar coating should be touched by contaminated materials. This arrangement has the advantage that agar film has less tendency to slip from slide whenever it is held by oversight too long in water, however the modification with double coating is not the preferred one, and the same applies to the slides having one side coated with an universal nutrient (such as the nutrient agar and the other side with a differential medium such as for instance MacConkey agar or Endo agar or some selective agar such as Bismuth Sulfite agar or desoycholate citrate agar alls these media may help in the identification of investigated bacteria and all are described in the "Difco Manual" published by Difco Labs., Inc. in Detroit, Mich. 9th edition, 1953. Although bacteria will be mentioned in many places in this specification, however, the same method and means can be used with most microorganisms such as ricketsia, molds, yeasts, fungi, larger viruses which can be retained on agar surface which has the pore sizes about 10-50 Angstroms depending on the concentration of agar drying rate and exposure to factors lowering the pore size such as heat at temperatures higher than 60°-70° C., ultra violet light and some other factors.

The described new method of distribution, depositing, and inoculation of microorganisms consists in bringing an aqueous suspension of tested microorganisms onto a surface of dehydrated film of hydrophilic polymer, (preferably agar, capable of forming a solid (non-flowing) gel on rehydration, said polymer present as an adhering coating on a support suitable for coating, drying and examination under a microscope at a magnification of preferably over 350×, said hydrophilic polymer absorbs the free water in aqueous liquid; said suspension of said microorganisms is filtered off and has its microorganisms distributed on the polymer's surface devoid of free water, thus fixing (immobilizing) said microorganisms on said surface, whereby said microorganisms are capable of growing in colonies and said colonies capable to be examined under a microscope preferably at a magnification of about 350× or higher or lower depending on morphology of given bacteria under investigation.

Based on the described inoculation method the inventor developed a method of determining or estimating the viable bacteria population in water, sewage foods or medical materials. As the preferred application of the inoculation method can be described as follows: the method of determining (estimating or counting) microorganisms population comprises following steps— spreading an aqueous dispersion of said microorganisms onto the surface of a dehydrated polymer film on the supporting microscopic slide said film capable of forming a solid gel on rehydration said film containing or devoid of nutrient for said microorganisms said supporting material being suitable for coating, drying and examination under transmitted or reflected light of said microorganisms or colonies said film containing optionally a coloring matter capable of discoloring when exposed to (in vicinity of) said microorganisms said film by imbibing water from said suspension functions as a filter to retain and distribute the microorganisms content of said suspension as a deposit (with or without natural nutrients present in said dispersion) on the surface of the said film thus fixed microorganisms (immobilized) being capable to grow in colonies when incubated at an appropriate temperature and humidity thereafter determining said microorganisms population by determining (if coloring matter was present) the discoloration degree either measuring the transmission of light or by measuring the time elapsed from the beginning of incubation (or other fixed time as a starting point) up to some fixed discoloration degree (e.g. first visible with naked eye discoloration or more objectively until desired discoloration degree established with a suitable color sensitive instrument like colorimeter or spectrophotometer), having previously determined the correlation between the discoloration degree with the bacterial counts determined by agar plating method, conventional, also called Standard Method.

A combination of the two above described methods is the preferred form of my invention whereby a small circle or square, or oval (or other shape), contains above indicated ingredients required to show a discoloration in the presence of microorganisms and thus gives a rapid determination of rough estimate of bacteria population, while exact data are given as an actual count of colonies taken from the microscopic examination and counting of the remaining surface of the agar medium, which may contain or be devoid of the coloring matter. In the latter case the count can be made electronically with a beam of color sensitive (connected with a color sensitive photocell) light. In this way the troublesome and tiring microscopic counting can be carried out whenever more detailed study of bacterial population is required, while the initial estimate by discoloring often gives the necessary warning and location of the contamination.

The procedure for total count of microorganisms is as follows: The microscopic slide (made of glass or transparent plastic such as celluloid, cellophane or urea formaldehyde resin or other synthetic resin like cellulose acetate, ethylcellulose, etc.) is covered with a liquid dispersion (preferably warm) of some preferably gel-forming hydrophile polymer or a mixture of polymers such as, for instance: agar, irish moss, iceland moss, gum arabic, gluten, zein, gelatine, pectin, algin, alginates, methylcellulose, carboxymethylcellulose, water soluble ethylcellulose, hydroxyethylcellulose, polyvinylalcohol, polyacrylic resin, urea formaldehyde resin, carob seed, quincy seed, gums of tragacanth, karya, karaya, guar, senegal, locust bean, gelled starch or modified starch, as well as any other water swelling hydrophile polymer. My preferred mixture is 3% agar with 1% of carboxymethyl cellulose high viscosity (CMC Hercules Trade Mark 70 D High). Another preferred dispersion is 3% agar alone in water. By microscopic slide is meant a well defined structure as used for observation under the microscope, i.e. a stiff, preferably rectangural, flat-piece of material made of a clearly transparent material (not merely translucent) conveniently suitable and regularly used for observations under the microscope. Petri dishes, paper strips and highly porous membrane filter (e.g. Trade Mark "Millipore") or similar structures are not intended to be meant by my term "microscopic slide". Thereafter the dispersion is allowed to cool down and set to a gel, then dried, for instance, at room temperature with dried air on a hot plate at 70° C. or 100° C. This way a film of said polymer is formed on the microscopic slide surface. The amount of the liquid dispersion used may vary considerably and should be chosen each time experimentally to avoid too great thickness and reticulation. With 3% agar I prefer to use about from 1 to 5 grams of dispersion per one side of microscopic slide 1 by 3 inches in dimension. The reticulation of the dried film on remoistening should be avoided by the well known technics employed in photographic plates preparation, while agar does not need any special treatments except that it should be dried when set in gel form and the same applies to other gel-forming polymers. Thereafter, by means of some water or alcohol soluble ink or paint or wax pencil (e.g. gravure printing ink, or water resistant wall paint (Trade Mark Kemtone) or regular red was pencil may be used) squares of 1 sq. cm. or 1 sq. inch (or other suitable measurement) are delineated on the coated surface or preferably on the opposite side on glass or plastic surface of the microscopic slide. After the ink or paint dries out, the plate is ready for viable or total bacteria counting. For this purpose a dilution of said food is prepared according to regular bacteriological technic. Thereafter, between 0.01 ml and 2.0 ml of said dilution (this can be larger or smaller) depending on the anticipated bacteria count and physical characteristics of the food and film coating) is spread evenly on the delineated surface of the plate (slide), and dried (for instance, on a hot plate at 70°-100° C.) or in a stream of a dry air at room temperature (15°-25° C. or thereabout). Due to the hydrophilism of the coated surface the water suspension spreads very easily and evenly on the surface of the delineated square, while the lines made with paint or ink prevent the suspension from spreading beyond the boundary of the square, (the paint or ink should have its surface considerably less hydrophile than that of the polymer or preferably even hydrophobe, i.e. water repellent). The spreading of the tested bacterial suspension can also be done by immersing (dipping) the microscopic slide or a part of it for a fraction of a minute (e.g. 1/10 second to 50 seconds) or longer, as determined experimentally, so that said suspension adheres to the dried polymer film evenly, but is not imbibed to a great extent into said film, because then the swollen film may detach itself from the slide. Thereafter on taking out the slide from said suspension its water is sucked in into the polymer film on said slide. The above mentioned delineating lines can also be stamped or drawn on the reverse side of the plate, which does not interfere with the spreading of the bacterial suspension. It is recommended to siliconize, treat with fat or hydrocarbon, (or otherwise make water repellent) the noncoated (reverse) surface of the microscopic slide, so that when it is dipped into an aqueous bacteria suspension the aqueous liquid will not adhere to the noncoated surface of the slide or will be easily shed off by slight shaking.

Before the microscopic examination the bacteria can be preferably stained with suitable dye and, for instance, with agar, the hemathoxylin and iron sulfate or acidified methylene blue can be used as described in the Tanner's Textbook "Microbiology of Foods" 2nd. Edition, together with the description of Frost Little plate or Frost-Nickerson Little plate.

It is however possible to observe the bacteria deposed on the surface of a polymer film entirely without staining when the intensity of illumination is somewhat decreased, or phase microscope is used. Bacteria appear this way quite distinctly under the microscope, so that even E. Coli can be recognized and individual cells counted under 450× magnification which is ordinarily possible only with great skill. The agar film is particularly suitable for this purpose while on a gelatine film the bacteria are barely visible at the same conditions. I explain this effect to the great stiffness of agar gel which is probably greater than the stiffness of the bacteria cell itself. When the water from the food suspension is imbibed into the agar layer then bacteria are held up on the surface of the agar gel. Being less stiff than the agar gel as well as being pressed toward its surface by the stream of water imbibed into the agar, the bacteria spread flat on the surface of the gel, whereby, on examination under microscope, they are more distinctly recognized sometimes appearing even larger than when prepared by the ordinary technic, when they actually shrink during the "fixing" operation with the flame. On the other hand, the gelatine gel being less stiff than bacteria itself (in my explanation) allow the bacteria to be imbedded into the gel layer, whereby bacteria become surrounded by the gel layer and become less visible under the microscope.

The above described effect is one more reason why agar is preferred for this invention. Besides, agar has been used in the microscopic and bacteriological technics since the beginning of bacteriology and accordingly, there are many well elaborated staining technics suitable for agar, while for other polymers the staining technics are not so well elaborated. Also, agar, as well as many other vegetable polymers (Irish moss, pectin) are less subject to bacteria growth on them when no nutrient is present and, for that reason, is particularly preferred for counting living bacteria when the plate is incubated. Nevertheless, other polymers which are subject to bacteria development such as gelatine, starch, may also be used with advantages for counting living bacteria by taking advantage of the modification they undergo due to bacteria metabolism, for instance starch may be modified and iodine will detect places modified, while litmus indicator may show acid formation by bacteria on gelatine. Accordingly, everywhere agar is mentioned, also other polymers can be used freely. For counting living bacteria in one modification, the procedure is very similar, except that a suitable amount of nutrient is incorporated into the agar layer. I prefer to use 10% of dried nutrient broth (e.g. Trade Mark "Difco") by weight of the agar used, however other amounts or other nutrients can be used depending on the characteristics of the bacteria in question. For instance, peptone, casein, lactose, sugars, blood, gelatine, starch, may be employed. As to the principle of selecting the amount of nutrient, see explanation below. Furthermore, the layer of agar should be thicker than mentioned previously and I prefer to use 4.5–10 grams of 3% agar (or its mixture with 1% carboxymethyl-cellulose, (high viscosity), per one side of the microscopic slide 1 by 3 inches in dimensions. The amount of the measured food dilution (suspension) which is spread over the delineated square is also greater in this count since otherwise the water tends to dry out during the incubation period. I prefer to use 0.05 ml to 0.1 ml per square centimeter. The amount of food suspension (its water content), the thickness of agar film (layer) and its content of nutrients should be so chosen by prior experiments, that when the water from the food suspension is imbibed into the dry agar film (which swells) at room temperature or at incubation temperature (i.e. usually 20°–45° C.) resulting gel layer contains optimum percentage of nutrient for bacteria growth. For instance, if 4.5 grams of 3% agar are spread over the surface of 1×3 inches and then dried, the resulting agar film will have about 0.75 milligrams of agar per square centimeter, and if 0.05 ml of water suspension is spread over this surface of 1 sq. cm. then the agar gel which will be formed (by imbibition of water into the agar film) will contain about 9.4% of nutrient, provided the initial agar had 10% of its weight of nutrient in it. I found these conditions optimal for the development of *E. Coli*, however, for other bacteria, other conditions may be better. In each case they should be determined by prior experiment and this requirement is not impractical since always in bacteriology the incubation conditions and nutrient requirements of given bacteria are determined prior to actual testing or population count. It discovered that in all cases the ratio of the nutrient weight to agar weight is very much lower (preferably at least 3× lower depending on actual experimental test) than in the corresponding, conventional nutrient agar mixture. Otherwise the bacteria do not grow or grow sluggishly on the agar gel swollen at room temperature or higher up to 80° C. (i.e. below the melting point of agar gel). For commonly encountered bacteria (soil type, water type, dust type, etc.) this requirement is not very strict since these bacteria grow in a great range of conditions. When the water from the food suspension is imbibed into the agar, (which happens after 10–15 minutes) gel, bacteria and food particles are collected on the surface of the agar gel, and it is important that the amount of water which is spread over the delineated square would be sucked into the agar to the last drop so that no free liquid remains on the surface of the gel. Otherwise, if some water remains not imbibed and floats on the surface of the gel, then the bacteria colonies have a tendency to spread excessively and merge, with resulting difficulties into counting. Sometimes it is practical to spread different amounts of water suspension over each square on a given plate (which may have 4–5 squares per plate) and later chose for counting only those cultures (squares) which had no spreaders, i.e. in which all of the water has been sucked into the agar gel. After "plating" (spreading), each plate is incubated at appropriate temperature in a moist chamber. As well known, all surface cultures of bacteria grow very rapidly as far as common aerobic bacteria are concerned and this is one of the reasons why this method is so rapid. Furthermore, since all the bacteria colonies are obtained after the incubation in approximately one plane (on the agar surface), therefore, they can be observed. After drying and staining, with a high power magnification under the microscope (e.g. 450× or 1000×). This enables the observation of each colony in its early stages of development; for instance, when one cell multiplies to 8–32 cells, and furthermore, it enables the counting of each cell in each colony.

The bacteria can be stained with suitable dye and, for instance, with agar, the hemathoxylin and iron sulfate or acidified methylene blue can be used as described in the Tanner's Textbook "Microbiology of Foods" 2nd Edition, together with the description of Frost Little plate or Frost-Nickerson Little plate.

It is however possible to observe the bacteria deposed on the surface of a polymer film entirely without staining when the intensity of illumination is somewhat decreased, or phase microscope is used. Bacteria appear this way quite distinctly under the microscope, so that even *E. Coli* can be recognized and individual cells counted under 350–400× magnification which is ordinarily possible only with great skill.

Polymers which are subject to bacteria growth on them alone (without added nutrients), such as gelatine, starch, may also be used for counting living bacteria by taking advantage of the modification they undergo due to bacteria metabolism, for instance starch may be modified and iodine will detect places modified, while litmus indicator may show acid formation by bacteria on gelatine. Accordingly, everywhere agar is mentioned, also other polymers can be used.

For counting living bacteria in one modification, the procedure is very similar to that described above, except that preferably a suitable amount of nutrient is incorporated into the agar layer and bacteria are incubated before counting. I prefer to use dried nutrient broth (e.g. Trade Mark "Difco") 10% by weight of the amount recommended in Difco Manual; however, other amounts or other nutrients can be used depending on the characteristics of the polymer (agar) or the bacteria in question. For instance, peptone, casein, lactose, sugars, blood, gelatine, starch, may be employed. As to the principle of selecting the amount of nutrient, see explanation below. Furthermore, the layer of agar should be thicker than mentioned previously and I prefer to use 4.5-10 grams of 3% agar. The amount of food suspension (its water content), the thickness of agar film (layer) and its content of nutrients should be so chosen by prior experiments, so that when the water from the food suspension is imbibed into the dry agar film (which swells) at room temperature or at incubation temperature (i.e. usually 20°–45° C.), resulting gel layer contains optimum percentage of nutrient for bacteria growth and all liquid (free) water is absorbed from said suspension. This requirement is not impractical since most bacteriological tests are done routinely on the same product and the incubation conditions and nutrient requirements of given bacteria are determined prior to actual testing or population count. I discovered that in most cases the ratio of the nutrient weight to agar weight is very much lower (preferably at least $3\times$ lower depending on actual experimental test) than in the corresponding, conventional nutrient agar mixture. Otherwise some bacteria do not grow or grow sluggishly on the agar gel. For commonly encountered bacteria (soil type, water type, dust type, etc.) this requirement is not very strict since these bacteria grow in a great range of conditions. When the water from the food suspension is imbibed into the agar, (which usually happens after 10–15 minutes), gel, if some water remains not imbibed and floats on the surface of the gel, then the bacteria colonies have a tendency to spread excessively and merge, with resulting difficulties in counting. Sometimes it is practical to spread different amounts of water suspension over each square on a given plate (which may have 4–5 squares or circles 1 sq. cm. each per plate) and later chose for counting only those cultures (squares) which had no spreaders, i.e. in which all of the water has been sucked into the agar gel. After "plating" (spreading), each plate is incubated at appropriate temperature in a moist chamber. As well known, all surface cultures of bacteria grow very rapidly as far as common aerobic bacteria are concerned and this is one of the reasons why this method is so rapid. When few dilutions are made and the tested liquid contains adequate amount of food in suspension and solution, (such as is often the case with milk), then it is possible to employ the coating of plain agar on the microplate without any added nutrients for bacteria. Then after spreading and imbibing the available natural nutrients (for bacteria), good ingredients will be partly imbibed into the agar and partly filtered off together with bacteria on the agar surface, so that all food ingredients will support satisfactorily the bacteria growth on incubation of so prepared microplates. The preferred method of spreading the examined suspension, if available in abundance (as e.g. milk, sewage or water), is to dip the slide into the examined liquid, as described in detail in the example at the end of the specification.

Furthermore, since all bacteria colonies are obtained after the incubation and drying in approximately one plane (on the even agar surface), therefore, they can be observed, after staining, under a high magnification of a microscope (e.g. $400\times$, or $600\times$, or oil immersion at $1000\times$). This allows for the observation of each colony in its early stages of development; for instance when one cell multiplies unto 8-32 cells, and, if colonies are young enough it is possible sometime to count the No of cells in each colony. In this way by counting and comparing plates incubated different times at the same conditions, not only the population of living bacteria, but also their viability (i.e. their speed of multiplication) can be determined at a low cost of equipment and labor. In addition, since the bacteria are visible under the microscope without staining, these surface colonies can be observed in living condition under $400\times$ or $600\times$ and their growth stages observed in great detail, and photographed, which was not feasible with prior art. Of course a stage incubator and a field finder should be employed for this purpose. After the appropriate incubation period in a moist chamber the microplates are dried either at room temperature (preferred because many bacteria survive after room temperature drying and such a plate can be after storage rehydrated and incubated or some microorganisms transferred to another culture medium and identified at a future time if need arises), in a stream of dried air or nitrogen, or they can be dried on a hot plate, (e.g. at 70° C.). Conventional staining follows with conventional total direct counting procedure. By comparing the count after incubation with a count on a similar npnincubated plate, (dried immediately after plating), the colonies which grew during the incubation can be estimated and thus, the number of living bacteria can be determined. The incubation time with the above described technique can be short e.g. $\frac{1}{2}$–4 hours; however by incubating for a longer time of 4–8 hrs or 4–6 hrs. the colonies could be grown to a such size that the distinction from dead bacteria clumps will be easy and running control, (nonincubated microplate), will be not necessary. The above described modification of determining the population of viable (living) bacteria requires the counting of colonies under the microscope, and this not only requires a professional, experienced bacteriologist, but also is tiring and awkward and constitutes the principal drawback of microscopic techniques for the determination of bacteria population. However, another modification offers a very important advantage, while retaining the accuracy of the plate count (in a Petri Dish), in that the counting under a microscope can be entirely eliminated, so that the determination can be performed fast by a nonskilled worker after only a short training. This modification can be described as follows:

This method is appropriately called: "solid state methylene blue test", although not only methylene blue but also other dyes as well as natural coloring matters, could be employed for this purpose. This method involves the determination of microorganism population either by measuring the degree of the discoloration, by determining the time period from e.g. start of incubation to beginning of discoloration, as effected by microorganisms of a dye such as methylene blue, resazurin, 2,3,5-triphenyl-tetrazolium chloride, blue tetrazolium chloride thymol blue, basic fuchsin-sulfite, brilliant green, bromcresol—purple, eosin, crystal violet, litmus, indigo, dye suitable and capable of discoloration when exposed to (in the vicinity of) viable microorganisms. The dye is incorporated into the said medium, for growing said microorganism, and said medium when liquid, is spread as an adhering film (or coating), then dried and thus obtained in dehydrated state (and preferably with a nutrient medium for said microorganisms) on a surface (preferably in one plane), of a material which will show said discoloration of the dye, such as a surface of of transparent glass or plastic (lucite, polystyrene, polypropylene, polycarbonate, etc.) or a nontransparent white or brightly colored glass or plastic (said color intended to show the discoloration more distinctly). Said dehydrated film is rehydrated with the aqueous suspension of tested microorganisms (such as in milk, water, or urine etc.), whereby the film imbibes water (free, liquid) from said suspension leaving the microorganisms filtered out on the surface of the rehydrated film. The microorganisms grow on this surface (in a moisturized incubator to prevent the drying out of the rehydrated film), utilizing the nutrient from said film and they discolor the dye primarily around each growing colony of said microorganisms. The beauty of said technical concept of spreading the discoloration on the surface is that it is adaptable for the automstic determination for instance by determining the extent of color appearance or change or color loss or fluorescence by means of a colorimeter or photometer or spectrophotometer or otherwise counting the number of discolored places on said surface can be used either manually, or by means of a scanning light beam, whereby as said before the debris will not distribut the counting of said debris being not able to effect the disoloration of said dye. Because the colonies should grow only to a microscopic size, therefore the incubation time is usually much shorter, a fraction of the time prescribed for the standard plate count. The thinner is the film on the microplate, the faster discolored colonies appear when viewed under a microscope. The fact that bacteria and their colonies are much better visible when located on the dehydrated agar film (as well as on rehydrated film), causes said discolored colonies to appear clearer when viewed through a microscope. For instance a photometer or spectrophotometer should detect even one small, red presumptive coliform colony on the observed field, or it should be able to determine the degree of discoloration (of the red or green, or blue component in the observed field). However the preferred method or to determine the time period (see above). An estimate can be accomplished with a single comparative colorimeter, whereby the color would be matched with several appropriately colored standardized color plates or an unused, similarly colored microplate. The drying should be preferably done with a dry air (dried with Calcium chloride or perchlorate, or calcium sulfate semi-hydrate). This preference is due to the possibility of storing dried plates for a future time when it should be possible to retrieve the microplate from storage and rehydrate it, cultivate the microorganisms and transfer them (after prior selection of desired colonies) by means of a micro-manipulator to a culture medium and thereafter examining and identifying them, with conventional procedures, in case storage is not desired, then microplate can be dried at higher temperature (e.g. such as 70°-100° C.) and the upper temperature of drying is limited only by scorching temperature of the coating on the microplate. However drying is not obligatory and the examination can proceed with moist film. The same exactly method could be used for the detection, identifying and counting of coliform bacteria and for this purpose the special media could be employed, such as Endo agar, Violet Red, Bile Agar, Desoxylate Agar, Brilliant Green Bile Agar, or Desoxylate Lactose Agar or etc. Also pathogenic bacteria can be automatically screened (e.g. during epidemics) by employing conventional selective media in gel form, which give discolored colonies of pathogenic bacteria (such as Salmonella, Shigella, Anthracs etc.). Furthermore the fluorescent-antibody technique can be used with my method, by anybody skilled in the art.

The nutrient medium should be preferably desalted prior to the use by dialysis or electro-dialysis, while the dye concentration should be determined in each set of conditions experimentally. As a starting point the following concentrations could be given: for methylene blue—1 part by weight per 100,000 to 200,000 weight parts of water, for resazurin the same, or for tetrazolium 1 weight part per 1,000 to 10,000 weight parts of water, or for basic fuchsin sulfite 7 weight parts per 100,00 weight parts of water plus 20 weight parts of sulfite of sodium. Sterile conditions are maintained during drying. Drying at room temperature, or below, increases the absorption power of the agar, so that it absorbs more water, than when dried at a higher temperature say 90°-100° C. It is recommended to siliconize or coat with Teflon (Trade Mark of DuPont Co.) or otherwise make water-repellent the edges and the noncoated side of the microplate so that water would not stick to them when dipping the slide into tested material.

By doing a total, direct (Breed) count on one microplate (nonincubated) a viable count (living bacteria) on another microplate additional valuable information can be secured as to the state and history of the bacterial population. Counts of bacteria, molds or fungi should be preferably correlated with standard plate counts so that counts obtained on a microplate could be converted into the standard plate counts in Petri dishes. The same applies to estimates.

I agree, that my method of distributing, depositing and inoculation is very simple and that the streak plate method is somewhat similar. However the reason that my simple modification of the streak plate was not tried for over 100 years (because the streak plate method was known still before the advent of Koch in bacteriology), is that nobody expected that such a simple modification of the streak plate will give so many advantages surprising in their variety, scope and importance. It was not obvious that the mere dehydration of agar film, and placing it on a microscopic slide, will give such surprising effects. The most important advantage can be stated as follows: when bacteria are deposited by the above described method on the surface of agar films, then they become enlarged and well visible even viable and without staining under a conventional light microscope (particularly when the density of the illumination is somewhat decreased). Of course with staining the visibility is still much better, so that *E. coli* could be examined and counted under 350–400× magnification which was very difficult with bacteria smeared on a glass plate (as done in the conventional total, direct (Breed) count). This effect of improved visibility under microscope obtained with my method is striking and of course of a great assistance in doing the counting early under microscope, when the incubated colonies are still small (after 1½–3 hours of incubation. This effect cannot be satisfactorily explained, and is probably connected with the surface tension of water, considerable resistance to penetration, resiliancy and the Refractive Index of agar film at the exceptionally high concentration of agar and/or completely dry as encountered on my microplates. Namely in average agar imbibes at room temperature, during less than one hour, from dry state only a limited amount of water—about 80% (some batches of other agar may absorb up to 90%), so that the agar on my microplates after rehydration at room temperature has not less than 10–20% of agar (per weight of water). The agar of this concentration cannot be prepared (as a film on a support) and used satisfactorily in a laboratory, because of too high viscosity even at 100° Centigrade. The highest concentration of agar which can be used (rarely and not conveniently) in a bacteriological laboratory is 6%. Consequently agar of 10–20% per weight of water (or higher) was never tried as a background for bacteria under a microscope, because nobody came to use my simple method of distributing, depositing and inoculating in which a highly concentrated agar is produced in one plane, as a smooth background for the examination under high magnification of over 350× through a microscope on a non-dried agar. Nobody expected that such simple modification of streak plate technique will give such surprising effect of improved visibility as well as many other advantages listed below.

(1) The filtering effect is highly efficient, because the higher is agar concentration in the polymer film the higher are capillary forces which suck in the water from bacterial suspension, and at the same time the smaller are pores on polymer's surface. Consequently, the filtering effect is much more efficient than in a streak plate where only 1–2% of agar is present in the medium.

Some other hydrophilic polymers listed above can be used with similar effect as a background with improved visibility for bacteria examination under microscope. These hydrophilic polymers suitable for my methods should have similar Refractive Index like 10–20% and/or dry agar, limited amount of water of 60–90% imbibed from a dry state, a solubility of about 1–25% in water at 100° C. with a formation of a solid gel on cooling, said gel having similar resiliancy and resistance to penetration like 6–30% agar, preferably 10–20%, sometimes up to 40%.

(2) Debris interference is practically eliminated in the preferred colorimetric modification of my method, so that the automatic counting with a scanning light beam can be performed reliably, while in prior art some of the debris were counted often as a bacterial colony.

(3) The counting under microscope can be entirely eliminated as subsequently described. Thus the most tiring and objectionable step, in microscopic methods, requiring a skilled bacteriologist, is eliminated.

(4) Microplates can be stored for a long time in a small place before and after test.

(5) The incubation time is short—1½–4 hours, sometimes up to 8 hours if larger colonies are required.

(6) The test can be done by a low-skilled worker.

(7) Low cost and convenience makes it possible to run simultaneous tests with several media and at different conditions, so that much information on pathogens, thermofiles, anaerobes, etc., can be available in a short time; this is impossible with streak plates or the standard plate counts, which require much longer time periods.

(8) Field testing is feasible due to small size and simple equipment.

(9) Growth conditions on the surface are uniform and favorable, while in a pour plate some deep-seated colonies grow much slower than those on the surface.

(10) The range of population tested is 600 to 600,000 bacteria per milliliter, so that ordinarily (e.g., with milk) few dilutions, if any, should be made.

(11) With the preferred inoculation by dipping about 0.5 to 0.7 ml or even more of the sample is picked up, which is about the same as in standard plate count, thus assuring a more reliable test, than with other microscopic methods.

(12) The gross evaluation of the contamination or purity of the tested material can be done by an experienced person with his naked eye, looking for the degree of discoloration estimating this degree from the time it took to start discoloration or degree of turbidity of the microplate after incubation, or alternatively under a magnifier. By counting and comparing plates incubated different times at the same conditions, not only the population of living bacteria, but also their viability (i.e. their speed of multiplication) can be determined. Besides, since the bacteria are visible under the microscope without staining, these surface colonies can be observed in living condition under 450× or 1000× and their growth observed in great detail, which was not feasible with prior art. By utilizing a stage incubator with a suitable humidifier (to prevent the drying out of the culture), the colonies on one plate can be counted during their progressive growth (e.g. every 30 minutes or every hour) and in this way, the viability can be determined with a single plate as well as the number of living cells and the whole procedure takes only a few hours which was not possible with prior art. After the appropriate incubation period in a moist chamber (similar to that described for Frost Little plate by Tanner in the above mentioned textbook), the plates are dried on a hot plate (at 70° C. for instance), and stained as described above with total count procedure. The grown colonies on the incubated plate can be counted by the regular microscopic technic. By comparing the count after incubation with a count on a similar nonincubated plate (dried immediately after plating) the colonies which grew during the incubation can be estimated and thus, the number of living bacteria in foods can be counted. For instance, all the colonies grown on the incubated plate above the average size of bacteria groups on the nonincubated plate can be established as originating from living cells (as usually estimated in the regular plate count one colony originates from one cell). It is important, however, to break up as much as possible the clumps of bacteria prior to plating so that the average size of clumps on the nonincubated plate will be distinctly smaller than the grown colonies on the incubated plate, thus facilitating the distinction. This breaking up of clumps can be done for instance in a Warring blender or in a sterilized, laboratory type homogenizer.

Another important advantage of the method for counting of living cells (and total counts as well) is the low number of dilutions required or even the entire elimination of dilutions. Usually there are 500,000 to 600,000 microscopic fields in one square centimeter under the oil immersion of 1000× magnification. Accordingly, when using 0.1 μl. of milk per one sq.cm. which has 50,000 to 60,00 bacteria per ml. we shall get between 5,000 and 6,000 bacterial colonies per sq.cm. of the miniplate. Therefore there will be approximately 100 fields per per one bacterial colony. Thus it is obvious that much larger populations of bacteria can be counted. This advantage makes the method particularly suitable for making estimates and screening on the spot with fresh milk, polluted water, urine sewage etc. including swabbing of food handling equipment. Coliform counts can be made with conventional media on the miniplate.

Actually the inventor obtained good growth of *E. coli* by the described method after 2-3 hours of incubation at 37° C., while with the sgar plate method 24-48 hours is required. The minimum time of incubation stated by Tanner for for Frost Little plate is 4 hours which is rarely obtainable. With my method colonies could be grown after 6-8 hrs. of incubation to a size that made it easy to distinguish colonies of viable bacteria from dead clumps.

Another modification of doing the total count for living bacteria is as follows: About 0.1 to 1% of water dispersion of a thickener (i.e. water soluble, non-gel-forming, at employed concentration, polymer such as methylcellulose, carboxymethyl cellulose, irish moss, tragacanth gum, gum arabic, iceland moss, hydroxyethyl cellulose, polyvinyl alcohol, polyacrylic resin, urea formaldehyde resin, and like polymers) is prepared and sterilized. Thereafter, suitable dilution of food suspension in this thickener solution are made in regular bacteriological technic. Then a suitable amount of nutrient broth for given kind of bacteria is added, whereby the amount should be determined by prior experiment in such a way that after the plating and sucking in of the water from said thickener solution, the remaining half-liquid layer on the top of the agar will have an optimum amount of nutrient for bacteria development. Further description will clarify this statement. After the food suspension dilution with thickener and nutrient is prepared it is plated on the delineated surface of agar on the above described plates. 0.05-0.5 ml. is usually taken, for instance. Thereafter, the plates are put into a moist incubation chamber in the same way as described above and left at an appropriate temperature for 1-3 hours. After 10-15 minutes, the agar sucks-in most of the water from the food suspension and on its surface remains a layer of a half-liquid suspension of thickener with bacteria imbedded in it and surrounded by a medium containing nutrient in proportions suitable for growth. In this way, a miniature agar plate is formed in which the conditions for growth are similar to that of a regular agar plate where some bacteria have strictly aerobic conditions (on the surface) and some microaerobic conditions (i.e. with restricted air supply below the agar surface). For this reason, this modification more nearly represents the conditions of growth in the regular agar plate and gives more wide ranges for bacteria development. The amount of the thickener employed in the original suspension should be chosen by experiment in such a way that, after sucking of the water into the agar, the remaining on the top half-liquid layer will have a viscosity high enough to prevent the movement of mobile bacteria in it. This depends, of course, also on the amount of food suspension plated on the delineated square. Nevertheless, even if some restricted movement of bacteria in the half-liquid layer is possible this is not disturbing and sometimes very helpful since bacteria in moving in the half-liquid layer leave behind a channel (which does not close itself because of the pressure of metabolic gases exuded by the bacteria). By counting the amount of these channels it is possible to estimate the number of mobile bacteria in the food.

There are numerous modifications possible for the above described method and thus description is not confined to the above stated examples but embraces all the modifications under the claims. For instance, anaerobic bacteria can be grown on these microplates by immersing them after preparation into oil or by spraying them with oil (paraffin or immersion oil). Also for anaerobic growth the slides can be overwrapped and heat sealed in an atmosphere of nitrogen or carbon dioxide into air impermeable and transparent film, such as Trade Mark "Mylar" (or other polyester film), paraffin or wax impregnated paper or suitably coated cellophane many of which are on the market. This way after incubation the growth of anaerobic microorganisms can be observed through the overwrap (even under the microscope) without disturbing the anaerobic conditions of the growth. To avoid the cumbersome overwrapping in an atmosphere of nitrogen or carbon dioxide the anaerobic conditions can be secured by overwrapping the slide very tightly so that practically all the air will be squeezed out from underneath the overwrap. In addition, paraffin, oil or similar inocuous liquid can be introduced in between the overwrap and the microscopic slide to eliminate air completely. Also, specific bacteria reaction or coliform bacteria can be determined as already described and other bacteria types can also be identified this way by employing known technics in the manner described.

Microscopic slides with agar coating can be wrapped each separately after sterilization or before into a cellophane or polyethylene bag and then sterilized, for instance, in the cold by ethylene oxide or by radiation. This way, when needed, they can be conveniently used in sterile condition, and so manufactured in a factory ready to use.

It was determined that the agar film on microscopic slides absorbs considerably more liquid if the drying is performed between 0° C. and 50° C., preferably at room temperature (usually 15°-22° C.). Still better absorption is obtained when the film is frozen and then freezedried in vacuum or in air at atmospheric pressure with air dried by molecular sieves, magnesium perchlorate, alumina or other strongly dehydrating agent (leaving e.g. 20 ml/l of moisture in the air). The freeze drying has, however, the disadvantage that the film is less transparent. This disadvantage can be partly obviated by smearing a few drops of oil on that portion of the film which will be investigated under the microscope. The film will become transparent where oil is imbibed. Also it is recommended to use an adhesive as described before to prevent detachment when freezing. Furthermore, with liquids, an easier way to perform the test is just dip the whole slide into the liquid, withdraw immediately or after a measured time (e.g. 1-100 seconds or longer) and then allow the liquid to be absorbed, eventually repeat the same operation again (in case the amount of liquid absorbed is inadequate), incubate in humid atmosphere, and count the grown colonies eventually after drying and staining.

For counting of living molds a following modification can be used: Molds grow slowly and in 3 dimensions and therefore they are not very suitable for high magnification (<400x) microscopic observation. However, flat growth of molds can be obtained by covering the rehydrated and inoculated slide with a thin air permeable film (such as noncoated cellophane, or cellulose acetate, or ethyl cellulose 1-3 inch thick). Molds do not metabolize cellulose, or its esters or ethers and will be forced to grow (at least initially) in 2 dimensions (flat) so that these can be observed under the microscope and counted.

The microscopic slides covered with agar film may be prepared in nonsterile conditions, if normal cleanliness is taken care of. When the slides are not prepared sterily, they should be sterilized individually just prior to the actual test by passing the agar film side several times over flame, the same way as it is done in "flaming" bacteria test tubes. Microscopic slides, as described, are most conveniently prepared in advance as an article of manufacture and sold to bacteriologists wrapped in sterile film, ready to use and prepared with a various selective media, if desired. This way, one of the big drawbacks of standard plate count or membrane filter technics is obviated whereby it is not necessary to prepare many nutrient mediums for checking of certain fastidious bacteria when more exact determinations are made. Much labor and equipment is thus saved. To add further to the economy and rapidity of this method, each microscopic slide has at least 3 and possibly 4 microplates (1 square centimeter each) so that a control and duplicate samples can be run concurrently on one slide.

The described method can be used also for the determination of antibiotic activity similarly as is done on a Petri dish with the so called cup method. The cup for our microplate should have 2-4 mm. up to ½ inch in diameter and the test goes the same way as described in respective text books. (see "Standard Method for the Examination of Dairy Products, Wm. G. Walter, 12th Edition, Publ. 1967, pp. 72-76)

It is recommended to remove crystallizable salts (e.g. by electrodialysis or by diffusion through a membrane into water) to remove such electrolytes as NaCl, Na$_2$SO$_4$, Na$_4$P$_2$O$_7$, etc.) from the nutrient medium which is incorporated into the agar film. Otherwise small crystals of these salts (left after drying of the film) may look like single bacteria under the microscope with an unstained preparation, (e.g. under phase microscope).

In addition, as described further down such tests can be performed which cannot be acomplished conveniently with conventional prior art methods.

To support the above statement I would like to indicate that prof. Paul A. Hartman on pages 68 and 69 of his monograph "Miniaturized Microbiological Methods" (Academic Press 1968) described my noncolorimetric method in detail and states that my method is so easy and convenient that it could well eliminate some objections raised against the Frost Little Plate and arouse again the interest in microscopic methods. The colorimetric modification of my method was not yet developed at that time and was not published while estimation of bacterial population according to my color development as described added much to make the method shorter and less troublesome (in particular the microscopic counting at high populations has been practically eliminated, unless an exact study is required.

The principal method of the here described invention is the novel method for the distribution, deposition, and inoculation of microorganisms on the surface of a dry solid hydrophilic polymer or a mixture of polymers, cape of forming a solid gel—with less than 97% of water, preferably less than 95% more preferably less than 90% and most preferably less than 80% of water, on rehydration from a dry state with less than 15% of moisture preferably less than 10% of moisture, and most preferably less than 5% of moisture (to prevent bacteria growth on accidental contamination in storage),—said solid gel having a similar resiliancy, resistance to penetration, and Refractive Index as those of 3% plain agar preferably of over 6% of plain agar, more preferably of over 10% plain agar, and most preferably of over 20% plain agar up to 40% (without admixture of any other gums). In addition to agar (sometimes called agar-agar), gums selected from the following group can be used with my method: Danish agar, otherwise called furcellaran, (agaroid gums originating from the sea), gelatine, gel forming Irish moss, carregein, carregeinates, pectin, pectinates, gluten, zein, gums capable of forming a solid gel and rehydration from a dry state and/or absorbing preferably a limited amount of water preferably during less than one hour of contact with water. Also some other gums not capable of forming a solid gel can be used as an admixture to above indicated gel-forming gums, as follows: carboxymethylcellulose (the preferred gum), methylcellulose, water-soluble ethylcellulose, water-soluble hydroxyethylcellulose, polyvinyl, alcohol, carbo seed, quincy and tragacanth gums, karaya, senegal, locust bean or their mixtures or other water dispersible polymer capable of forming viscous solutions with similar viscosity as 1% solution of CMC-70D High (Hercules Co. Trade Mark for carboxymethylcellulose-high viscosity). Said solid gel forms a film on a support, suitable for coating, drying, and observation in transmitted or reflected light under a microscope with a magnification preferably above 350× and more preferably at or under 600× and most preferably at or under 1000× with oil immesion. The following materials for the support are suitable: borosilicate (preferred), or sodium (soft) glass, stiff fiber glass, urea-formaldehyde resin, phenol-fordehyde resin, celluloid, hydrated cellulose, cellulose acetate, water insoluble etother synthetic water insoluble resins capable of forming a flat, smooth microscopic slide retaining the required mechanical strength when wet, (preferred size 1×3 inches) transparent or translucent or reflecting, so that microscopic bacterial colonies will be well visible preferably under microscope, as indicated above; although lesser magnification can also be used for evaluation purposes, where morphology of bacteria does not need to be established, (even naked eye can be used for gross evaluation of the discoloration degree, or turbidity of the incubated microplate). It should be noted that from a dry state agar and other gel forming polymers absorb water initially at a fast rate, which rate slows down with passage of time of contact with water, until the absorption rate slows down so much that it is for practical purposes (in my method) not existent. During the specified time of one hour of contact time with water agar on average absorbs 80% of water, although being a product of nature batches of commercial agar cannot be standardized and the amount of water may vary as much as 70 to 90% and larger variations are feasible although not encountered in my practice.

Furthermore a flat growth of molds and fungi can be obtained by covering the microplate shortly after incubation with an oxygen permeable film (such as cellulose acetate, or noncoated hydrated cellulose (cellophane). This film will restrain the upward growth of molds and fungi so that these can be counted and their morphology determined, doing all this under a microscope (350× or higher although also lower magnification could be used) much earlier than possible with prior art methods.

The preferred means for carrying out the method with the film coated, flat surface is the transparent glass, microscopic slide 1×3 inches in size (conventional microscopic slide), which is coated on one side with the dehydrated agar with or without nutrient for microorganisms, capable of forming a solid gel on rehydration from a dry state, and optionally containing a coloring matter capable of discoloring in the vicinity of a viable microorganism, said gel capable of absorbing about all free, liquid water from the bacteria suspension to be examined, thus fixing bacteria and making them capable to grow in colonies, while making them at the same time exceptionally well visible under a microscope.

The preferred procedure in the preparation of microplates is to pour ½-10 ml. of 1-5% agar (preferably special agar noble (di) or deionized agar) (preferably 1-5 ml., of 3% agar containing one tenth up to half of the concentration of the recommended by Difco Manual concentration of a salt containing medium (or preferably a full, recommended concentration of a desalted nutrient medium), on the microscopic slide 1×3 inches in size made from borosilicate glass, then allowing said agar to set into a gel and then dry the film in a stream of air or nitrogen dried by passing over magnesium perchlorate, or calcium sulfate semihydrate, or other suitable drying agent. All this done at room temperature or below. The air should be sterile and microplate protected from contamination. The coloring matter, if at all desired, should be added either before coating to the medium, or after dehydration but before incubation the uncolored microplate can be dipped into the aqueous solution of said dye for previously selected time and dye concentration.

At this point I would like to give an explanation tentative in character which however should not be regarded as limiting in any way the invention. Namely the exceptionally improved visibility after plating on my microplates may be ascribed to the great stiffness of the agar at the concentration of 10-30% or higher as encluntered on my microplates after absorption of all the water from bacteria suspension. I assume that this stiffness (resistance to penetration) and resliency of such an agar is greater than the same properties of the bacteria cell. At the same time the considerable surface tension of the water plays a part in the great visibility effect. Namely when the water being absorbed streams into the agar gel it presses bacteria cells strongly (by virtue of its great surface tension) to the surface of the agar, so that bacterias spread flat on this surface, whereby on examination under microscope they appear larger, than when prepared by conventional technique when they may actually shrink during the "fixing" operation with the flame or chemical action. Also the refractive index of the agar may be highenough to cause an improved visibility of bacteria similarly as in oil immersion, techique.

It should be noted that my preparation of the agar gel for microorganism culture and examination under a microscope is quite different to the conventional preparation of the agar gel for Petri dishes or other culturing techniques used conventionally in bacteriological laboratories. Namely at present in laboratories the water-agar system, as used in preparing the aqueous solution of the agar, contains as a rule 1-2% of agar and 98-99% of water (disregarding adjustements due to inclusion of nutrients, dyes etc.). This mixture is heated to about 100° C. and a 1-2% agar solution in water results, which is now cooled to 45°-60° C. and acteria suspension is added whereupon this culturing medium is poured into Petri dishes. Alternatively, with the streak plates the noninoculated agar medium is allowed to set to a gel before incoculat in whereupon the incoculation is performed with a loop or brush, by streaking. In my method all the procedure of inoculation and agar gel preparation on the miniplate is performed at room temperature and the agar-water system contains about 20-30% agar (or sometimes 10-50% agar) resulting in a hydrated agar medium containing approximately 20-30% agar (or 10-90% agar depending on proportion of given growth of agar). It is obvious that the conventional way of preparing the culturing medium is completely different from my method, and the same applies to the inoculation method. These differences are so great that both methods cannot be compared, especially that the fact of getting so highly concentrated agar in my method is of material importance to visibility and some other new effects produced. It should be noted that this high visibility occurs both with dry agar as well as with the wet agar film (before drying), so that both living as well as dead or dormant bacteria can be observed with improved visibility.

It should be also noted that some gel forming (substances) polymers which absorb more than 90% of water during one hr of contact, such as for instance calcium alginate, can be also used with my method, whereby the amount of water in bacteria suspension plated on the microplate is restricted so that the ratio of water to dry calcium alginate (or other polymer) is the desired ratio (e.g. 90:10 or 80:20 or 60:40 or otherwise).

Furthermore it should be noted that everywhere where staining is mentioned in the specification it is intended for the observation under microscope and the preferred stain for this purpose is so called Loeffler's stain diluted 3× with distilled water, as described in Tanner's (Fred Wa.) in his Laboratory Manual and Work Book (Garrard Press, Champaign, Ill. 1950) pn page 1, Section 3, Chapter 6, "Milk". However most conventional stains for particular bacteria and media can be used.

The following improvements and alternatives may be incorporated as opoptional matter:

A nontoxic (at conditions of use) to bacteria surface active agent may be added to the medium before plating (coating) at a preferable concentration of 0.05 to 0.5 wt.% per medium weight (including water). Smaller or higher concentrations could be used and in each case the right concentration should be determined experimentally. The presence of a surface active agent accelerates (from the usual time of ¼-15 minutes), and increases the imbibition of water.

Some suitable adhesive can be incorporated between the coating (polymer film) and the microscopic slide, such as for instance a sodium, potassium, calcium or magnesium salt of resinuous acid, carboxymethylcellulose, methylcellulose, "Oxo" resin (Trade Mark of Union Carbide Corp.), or like adhesive. Alternatively grooves (1-2 mm deep) can be made on the to be coated surface of the slide to prevent slippage of the agar film. other adhesives which would stick to the hydrated coating of the hydrophilic polymer and to the glass as well such as for instance an adhesive for dentures or like and do not affect adversely microorganisms at conditions of use. This adhesive layer prevents the slipping off of the coating after it has been fully hydrated and also if freeze-drying of the polymer film is performed the adhesive prevents the peeling off of the polymer film after it gets frozen. The freeze drying increases considerably the speed of rehydration and increases the amount of water absorbed, although the transparency is not too satisfactory. It is possible of course to coat only part of the microscopic slide, leaving the noncoated part for holding with sterile fingers or forceps. It is preferable to freeze-dry not in a vacuum, but in a steam of dried air or nitrogen, or like with the dew point below the drying temperature. Also both sides can be coated (with some medium) by dipping. Both sides can be coated with two or more different media. Two or more media can be coated on one side only.

Four or five squares or circles each one square centimeter or square inch in surface can be delineated on the noncoated side of the microplate and then e.g. 0.03–0.4 ml. of tested suspension could be spread with a pipette tip or similar utensil on each square or circle and then the count or estimate can be done on the basis of only a fraction of a milliliter. This procedure is less exact than the dipping method, and the latter is preferred.

Another alternative for dipping procedure is to pour 0.5–1.0 ml. of tested material onto a level microplate and spread the material over the whole slide by means of e.g. side of the pipette "rolling" or "pushing" the liquid material on the surface. This procedure is also the preferred one and has the advantage of avoiding weighing and having the amount of tested material closer to 1 ml. and measuring this amount exactly.

Furthermore a flat growth of fungi or molds can be obtained by covering the microplate shortly after spreading the bacteria suspension with an oxygen permeable film (such as cellulose acetate or noncoated cellophane).

On the contrary using an oxygen impermeable film such as aluminum foil or polyester film), in the same way as with oxygen permeable film anaerobic culturing conditions could be produced and the count or estimate of anaerobic bacteria could results.

Half anaerobic conditions could be obtained by adding 0.05–0.2 wt.% per total weight of rehydrated medium or 0.005–0.025 wt.% of cystine on same basis as in the first instance adding sodium thioglycollate and in the second instance cystine. Afterwards the procedure is the same as described above for the first modification of viable bacteria count (without coloring matter addition).

Conventional fluorescence-antibody technique is particularly suitable as an application of my colorimetric modification of my method in that the amount (intensity) of the fluorescence or only points of fluorescence within the microplate can be easily determined. This way the presence of pathogens can be counted fast or estimated in a given food or medical material; even if such a test may only be a presumptive test, even so it may be of considerable value.

It is preferable to remove sodium chloride or other crystallizable substances, since otherwise bacteria may be inhibited in their growth or crystals of salt or other substances may look deceptibly like bacteria if viewed before staining them.

It is preferable to add the coloring matter to the melted polymer medium, however, it is possible to add the coloring matter by coating the microscopic slide without incorporating the coloring matter into the medium being coated, then drying the coating and then dipping the coated slide into a coloring matter solution. (dissolved in water, alcohol, acetone gasolene etc.) The coloring matter's aqueous solution can be applied before drying the coating The use of coloring matters in nonaqueous solution after drying has the advantage of being able to use coloring matter insoluble in water, provided the coloring matter is not toxic to bacteria, at conditions of use. (see above)

In order to prevent the slipping off the agar film, (whenever it is kept too long in an aqueous liquid (i.e. for longer than required of 60 seconds) to 3 minutes) it is recommended to use an adhesive as already described or alternatively to coat the slides on both sides either on the whole surface of the slide or only on a part of it to the dipping depth of few millimeters whereby gar with nutrient or without nutrient is being coated on one side (as already described) and the dipping for few millimeters is done afterwards, so that the additional coating for few millimeters (from both sides one inch in width) hold the agar film firmly in place. The preferred way of microplate (miniplate) structure is that coated on one side only and provided with a thin coating of cellulose adhesive (e.g. carboxymethylcellulose or methylcellulose underneath the agar film applied prior to the coating with the principal agar coating.

The preferred form of the invention (method) is to prepare single side-coated miniplates with or without nutrient in the agar coating dry the minislide at room temperature with dry air (or other gas like nitrogen carbon dioxide etc.) ten dip the miniplate into tested milk for 60 seconds and incubate at 37° C. then determine the time when the square or circle containing 2-3-5-triphenyl-tetrazolium chloride or other suitable dye capable to discolor in the presence of microorganisms said circle or square being placed on the surface of the slide before agar coating procedure (whereby the square or circle being approximately twice thicker than the agar coating and thus protruding above the agar surface), said time is counted from the beginning of incubation or from other moment as provided when the correlation between this time and the bacteria population as determined previously. After making thus an estimate of bacteria population the incubation is continued for necessary time to grow colonies to a suitable size and an exact count of these bacteria can be made. If desired, by observing and counting bacteria under a microscope with appropriate magnification depending on the extent and temperature of the additional incubation after the estimate.

The following dyes capable to discolor can be used but less preferably than tetrazolium dyes indicated above: blue tetrazolium 2-(p-iodophenyl-3-(p-nitrophenyl)-5-phenyl-tetrazolium chloride, methylene blue, reasazurin, fuchsin, decolorized with sodium sulfite, (as in Endo agar), brilliant green; of course not only nutrient agar medium but most of the media (differential, inhibiting some bacteria like violet Red Bile Agar, or desoxycholate agar, thioglycollate agar medium, and as despenassay base agar medium for the assay of antibiotics and most media (solid) described in the Difco Manual (see above).

In those instances where a gas formation is helpful in the indentification of the kind of bacteria present, then after the inoculation the microplate can be covered with a viscous (e.g. 100,000 cps centipoises or less e.g. within the range 1000–15000 cps) solution of carboxymethyl cellulose or other viscous solution of substances listed as an additive to gelforming polymers listed above. This viscous layer prevents the escape of gas from the growing bacteria, forming bubbles if bacteria are nonmotile, and channels, if bacteria are motile. This gas can be identified by conventional microchemical methods or by modern gas chromatography methods. This identification of gas can be helpful in identifying kind of bacteria present especially when the amount of bacteria material is too small for conventional identification procedures.

The following example is given for the illustration of my preferred modification of the distribution, deposition and inoculation method:

EXAMPLE #1

One side of the microscopic slide (1×3 inches in size) is coated with 5 ml. of a 3% agar plus 1% of carboxymethylcellulose, high viscosity ("CMC)-High" Trade Mark of Hercules Co.) plus 0.05% of bacteriological peptone and plus 10 weight % of 0.01% solution of methylene blue. Thus coated slide is dried at room temperature in a stream of air dried by passing through a layer of molecular sieves or magnesium perchlorate or calcium sulfate semihydrate. Nitrogen or other gas, could be used instead of air for drying. Before using the microplate it is weighed and the weight recorded. The handling should be sterile. The weighed microplate is taken with sterile forceps and dipped for 1-30 seconds (or longer) into the tested suspension of bacteria (milk for instance), which is agitated before dipping. Any fluid adhering to microplate on edges and on noncoated side is wiped off sterilly. It is recommended to siliconise or coat with Teflon (Trade Mark of du Pont Company), edges and the noncoated side so that water will not adhere to these parts. The microplate is again sterilly weighed (for the determination of the amount of the bacteria suspension picked up), and immediately put into the humidified incubator, at relative humidity of close to 100%, whereupon in about 10-15 minutes the aquous liquid from the bacteria suspension is absorbed into the agarlayer. After 2-4 hours of incubation at the temperature prescribed for the given test (e.g. 31° C.) the viable bacteria grow into small colonies around which the methylene blue is completely or partly discolored. The microplate is dried at room temperature in a stream of dried air or nitrogen similarly as described above in this example. The degree of color change can be determined with a simple comparative colorimeter using standarized microscopic slide similarly coated and showing various degrees of discoloration corresponding in total transmission to various bacteria populations of bacteria. This standarized control microplates can be correlated to results on standard plates (in Petri dishes), so that the whole estimate can be done by a comparatively low skilled worker., especially if recording comparative electrophotometer is used thus leaving a record of the test. Alternatively the discolored colonies can be counted by means of a scanning light beam, whereby no interference should be encountered from any debris present on the microplate. So prepared microplates can be stored for future use, if desired. If more information is desired then an experienced bacteriologist can decolorize the microplate and stain again, then examine bacteria for their morphology, or count the colonies again.

Numerous modifications for the above methods and means are not described herein, and the invention is not confined to the above described methods and means, but embraces all the modifications covered by the wording of following claims.

EXAMPLE #2

Another modification of the described method consists in distributing the amount of the examined aqueous suspension of microorganisms in exsess of that amount which can be absorbed by the said dehydrated polymer film, so that, after allowing the free, liquid water to be absorbed by said film, there will remain some amount of the free, liquid water on top of the film, with all the microorganisms in contact with this excess of water (part of microorganisms will be suspended and part resting on the top of the film). It is preferable that for ease of handling that this excess of water be absorbed during the later stages of the incubation (e.g. in the second half of the incubation period); however the excess of this free, liquid water may not be absorbed completely during the incubation. The coloring matter capable of discoloring when in the vicinity of viable microorganisms can be added at any suitable stage before the incubation or at early stages of the incubation (e.g. during the first hour). Substances to which the said coloring matter could be added can be listed in the following group: said growth medium before coating stage, water used in the preparation of the examined aqueous suspension of microorganisms, said examined suspension of microorganisms, the polymer coating (film) on the microplate, with or without microorganisms, either dry of containing water, the substance capable to bring into contact the aid coloring matter with said microorganisms. The advantage of this modification is that the discoloration proceeds faster when free liquid water is present, so that the discoloration of the said coloring matter will proceed in 1-8 hrs of incubation depending on bacteria population and the population of said microorganisms can be determined by determining the time to color change or the discoloration degree or transmission of light with the microplate after incubation, by either comparing the incubated plate with similar microplate nonincubated, or with a standarized series of color plates, which have been previously standarized to correspond with standard plate counts of similar examined suspension of micoorganisms. Alternatively, a calibration curve can be prepared in advance linking the time or the transmission of light to the standard plate counts of similar microorganisms and the respective population estimate can be read in few minutes from this curve, or the respective photometer can be calibrated in terms of the population figures. According to this modification (which is not the preferred one) the handling of microplates with free, liquid water on the top is inconvenient, if the whole surface of the microplate is covered with water; however with only one square centimeter, the handling is not too awkward, and the rapid results obtained make this modification appealing.

In order to prevent the handling of microplates with liquid on the top (which is inconvenient) it is recommended to put a porous, absorbent sheet on the top of the agar layer preferably with pores considerable larger than the bacteria size, such as conventional filter paper, or porous, hydrophilic sheet of some plastic, like hydrated cellulose, (cellophane), cellulose acetate, polyurethane film, or other sheet of material that is easily imbibed with water or aqueous suspension of bacteria). It is preferable (because of convenience) permanently (preferably) to attache this sheet to the agar film This can be achieved in different ways. one of which is to cool the sheet to $-5°$ to $+5°$ or thereabout below $+40\%$ and have the coated micro copic slide hot (above the setting temperature of the agar or other polymer preferably at 50°-70° C. lying on a hot plate or insulation so that the agar will remain loquid when the porous sheet will be placed on the agar surface. Than the agar could be cooled by a stream of cold air (at 0°–10° or below 30°–40° so that will set before the porous sheet will have time to imbibe much of the agar solution, but will form a firm bond with the porous sheet. When inoculating the microplate the porous sheet will absorb aqueous suspension of bacteria and pass through this suspension with bacteria toward the agar layer underneath. The bacteria will be retained on agar surface while the water will be imbibed partly by the agar layer with excess water (with bacteria) rejaininb in th porous sheet. For this urpose it is recommended to dip the microplate into the bacteria suspension for a longer period, such as 10–15 monutes) or place a larger amount of bacteria suspension on a delineated place on the microplate(such as e.g. 0.1–0.2 ml. per s q. cm.) Both the agar layer and the porous sheet should be of course impregnated pior tplacing of bacteria suspension with a experimetally determined amount of methylene blue or other syutablr dye capable of duscoloring when in the vicinity of viable bacteria. Therafter during the incubation of such a microplate methylene blue will discolor faster than when present inside of the ggar gel (film), because theis discoloration proceeds faster in liquid phase.

I claim:

1. The method of estimating a bacterial population which comprises (a) uniformly coating one surface of a transparent microscope slide with a film of a liquid dispersion of a nutrient for said bacteria and a hydrophilic polymer in an amount to form when dried a substantially uniform layer adhering strongly to the surface of the slide, (b) drying the said film at a temperature of between $-195°$ C. to $100°$ C., (c) evenly spreading a measured volume of an aqueous dispersion of a bacteria and nutrient containing material to be examined directly onto the surface of the dried film, (d) allowing the water of said aqueous dispersion to be imbibed by the said dried film whereby the bacterial content of said material is deposited directly onto the surface of the film, (e) incubating the slide containing the bacterial deposit to accelerate the growth of colonies thereof, and then (f) estimating the bacterial population.

2. The method of estimating a bacterial population as defined by claim 1 wherein the hydrophilic polymer is transparent when dried.

3. The method of estimating a bacterial population as defined by claim 1 wherein the dispersion of hydrophilic polymer includes a nutrient for the bacteria.

4. The method for estimating a bacterial population as defined in claim 1 wherein the hydrophilic polymer is agar.

5. The method for estimating a bacterial population as defined by claim 1 wherein the layer of agar includes a nutrient for the bacteria to be counted.

6. The method of estimating a bacterial population which comprises (a) uniformly coating one or both of the largest surfaces of a slide for microscopic examination with a film of a liquid dispersion of a nutrient for said bacteria ad a hydrophilic polymer in an amount to form when dried a layer adhering to the surface of the slide (b) drying the said film at a temperature between $-195°$ C. to $+100°$ C., (c) distributing evenly, a measured volume of an aqueous dispersion of bacteria and nutrient containing material to be examined onto the surface of the dried film (d) allowing the water of said aqueous dispersion to be imbibed by the said dried film, whereby the bacteria content of said material is deposited onto the surface of the film, (e) incubating the slide containing the bacterial deposit to achieve growth of colonies thereof, and then (f) estimating the quantity of bacterial colonies.

7. The method of counting bacteria as defined in claim 6 comprising the drying of said film at a temperature range within $0°$ C. to $60°$ C.

8. The method of estimating bacteria population which comprises (a) uniformily coating one or both largest surfaces of a slide for the examinati under microscope with a film of a liquid dispersion of a nutrient for said bacteria and a hydrophilic polymer in an amount to form when dried a layer adhering to the surface of the microscopic slide, (b) drying said film at a temperature between $-6°$ C. to $+100°$ C. (b) adding to said polymer before, during or after drying at a temperature between $-60°$ C. to $+100°$ C. a coloring matter capable of discoloring when being in the vicinity of viable microorganisms (c) distributing an experimentally estimated amount of an aqueous dispersion of bacteria and nutrient containing material to be examined onto the surface or surfaces of the dried film, (d) allowing the water of said aqueous dispersion to be imbibed by the said dried film, whereby the bacterial content of said material is deposited onto the surface or surfaces of the film, (e) incubating the slide containing the bacterial deposit to achieve growth of colonies thereof and discoloring the said coloring matter (f) estimating the quantity of bacterial colonies by measuring the time elapsed from the beginning of incubation to the first observable discoloration or by determining with known methods of the discoloration degree of said coloring matter.

9. The method of observing the form and growth stages of microorganisms and colonies thereof using a microscope provided with a humidified stage incubator and a field finder and carrying out the following steps: (a) coating a microscopic slide with a uniform film of liquid hydrophilic polymer dispersion polymer, capable of forming form a gel, (b) drying said film, (c) distributing an aqueous dispersion of a bacteria and nutrient containing material onto the surface of the dried film, (d) allowing the water of said aqueous dispersion to be imbibed by the said dried film, (e) incubating the slide containing the bacterial deposit to achieve growth of colonies thereof, (f) observing the growth stages of bacteria and colonies which are rendered especially clearly visible when viewed through a microscope while being positioned on the surface of the hydrophilic polymer.

10. The method of estimating bacterial population as recited in claim 6 wherein said coating contains coloring matter which changes color when acted on by viable bacteria and estimating the bacterial population by the degree of color change.

11. The method of estimating a bacterial population as recited in claim 6 wherein only a part of said coating contains coloring matter which changes color when acted on by viable bacteria and estimating the bacterial population by the change in the degree of color change.

* * * * *